United States Patent
Furuta (10) Patent No.: US 10,098,528 B2
(45) Date of Patent: *Oct. 16, 2018

(54) ILLUMINATION DEVICE

(71) Applicant: OLYMPUS CORPORATION, Tokyo (JP)

(72) Inventor: Koichiro Furuta, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 223 days.

This patent is subject to a terminal disclaimer.

(21) Appl. No.: 14/973,252

(22) Filed: Dec. 17, 2015

(65) Prior Publication Data

US 2016/0100750 A1     Apr. 14, 2016

Related U.S. Application Data

(63) Continuation of application No. PCT/JP2014/066700, filed on Jun. 24, 2014.

(30) Foreign Application Priority Data

Jul. 9, 2013  (JP) ................. 2013-143679

(51) Int. Cl.
  *F21V 7/04*    (2006.01)
  *F21V 11/00*   (2015.01)
  (Continued)

(52) U.S. Cl.
  CPC ........ *A61B 1/0615* (2013.01); *A61B 1/00096* (2013.01); *A61B 1/0607* (2013.01); (Continued)

(58) Field of Classification Search
  CPC . A61B 1/0615; A61B 1/00096; A61B 1/0607; A61B 1/0623; G02B 5/0205; G02B 5/0242; G02B 23/2469
  (Continued)

(56) References Cited

U.S. PATENT DOCUMENTS 6,293,910 B1   9/2001  Yamakita et al.
2008/0242935 A1  10/2008  Inoue
(Continued)

FOREIGN PATENT DOCUMENTS

EP   0904725 A1   3/1999
EP   2353490 A1   8/2011
(Continued)

OTHER PUBLICATIONS

International Search Report, dated Sep. 16, 2014, issued in corresponding International Application No. PCT/JP2014/066700.
(Continued)

*Primary Examiner* — Anh Mai
*Assistant Examiner* — Jessica M Apenteng
(74) *Attorney, Agent, or Firm* — Hunton Andrews Kurth LLP (57) ABSTRACT

An illumination device according to the present invention includes a light output unit having an output end that outputs illumination light; a diffusion layer that is disposed in a circumferential direction centered on a predetermined axis and that receives the illumination light from the output end, guides the illumination light while diffusing the illumination light, and outputs the illumination light from a surface thereof; and a reflective layer that is provided adjacent to a surface of the diffusion layer at an inner side in a radial direction and that reflects the illumination light outward in the radial direction. The diffusion layer contains a light guide material that guides the illumination light and a diffusion material dispersed and supported in the light guide material.

23 Claims, 7 Drawing Sheets

(51) Int. Cl.
    *A61B 1/06*         (2006.01)
    *G02B 5/02*         (2006.01)
    *G02B 23/24*       (2006.01)
    *A61B 1/00*         (2006.01)

(52) U.S. Cl.
    CPC .......... *A61B 1/0623* (2013.01); *G02B 5/0205* (2013.01); *G02B 5/0242* (2013.01); *G02B 23/2469* (2013.01)

(58) Field of Classification Search
    USPC ........................................................ 362/558
    See application file for complete search history.

(56) References Cited

U.S. PATENT DOCUMENTS

| | | | |
|---|---|---|---|
| 2011/0184244 A1 | 6/2011 | Rupasinghe et al. | |
| 2012/0051693 A1 | 3/2012 | Yoshida et al. | |
| 2013/0100696 A1* | 4/2013 | Brick .................. | F21K 9/00 362/603 |
| 2013/0287380 A1* | 10/2013 | Thursby ............. | E21B 47/0002 396/19 |

FOREIGN PATENT DOCUMENTS

| | | | | |
|---|---|---|---|---|
| EP | 2649923 A1 | 10/2013 | | |
| JP | H11-76148 A | 3/1999 | | |
| JP | 2004-329700 | 11/2004 | | |
| JP | 2008-237790 A | 10/2008 | | |
| JP | 2010129282 A | * 6/2010 | ............... | F21K 9/00 |
| JP | 2011-147757 A | 8/2011 | | |
| JP | 2011-152371 A | 8/2011 | | |
| JP | 2012-50607 A | 3/2012 | | |
| JP | 2012-55342 A | 3/2012 | | |
| JP | 2013-000387 A | 1/2013 | | |
| WO | WO 98/035607 A1 | 8/1998 | | |
| WO | 2012-137737 A1 | 10/2012 | | |

OTHER PUBLICATIONS

Office Action dated Jul. 11, 2017, in corresponding Japanese Patent Application No. 2013-143679 (English-language machine translation provided).

Office Action dated Feb. 23, 2018, in corresponding Japanese Patent Application No. 2013-143679 (English-language machine translation provided).

* cited by examiner

ILLUMINATION DEVICE

CROSS-REFERENCE TO RELATED APPLICATIONS

This is a continuation of International Application PCT/JP2014/066700, with an international filing date of Jun. 24, 2014, which is hereby incorporated by reference herein in its entirety. This application claims the benefit of Japanese Patent Application No. 2013-143679, filed on Jul. 9, 2013, the content of which is incorporated herein by reference.

TECHNICAL FIELD

The present invention relates to illumination devices, and particularly to an illumination device for use with endoscopes having viewing angles of 180° or more.

BACKGROUND ART

There is a known endoscope that has a wide viewing angle, i.e., 180° or more, and that allows simultaneous observation of forward, side, and even backward fields of view (see, for example, patent literature PTL 1 below). For example, if an endoscope having a viewing angle of 180° or more is used in the large intestine, where numerous folds are found, the back side of a fold can be observed without changing the orientation of the distal end of the endoscope by a large amount, which allows the user to manipulate the endoscope more easily and to find an affected area more reliably. The endoscope in PTL 1 has, at the distal end thereof, an illumination device including two light guides and illuminates forward and side fields of view with different light guides to illuminate a wide field of view in its entirety.

Endoscopes have various components concentrated at the tips thereof, including image-capturing optical systems for capturing images of subjects, channels for surgical instruments, nozzles for lens cleaning, and mechanisms for bending sections thereof. Accordingly, there is a need for an illumination device that can be installed in a thin endoscope within the minimum possible space in the radial direction. The illumination device in PTL 1 includes a plurality of light guides arranged side-by-side in the radial direction in the surrounding part of the image-capturing optical system, and the distal end of the light guide for side illumination is bent in the radial direction of the endoscope to achieve side illumination. This requires a large installation space in the radial direction of the endoscope and thus results in a large increase in the tip diameter of the endoscope.

CITATION LIST

Patent Literature

{PTL 1}
Japanese Unexamined Patent Application, Publication No. 2004-329700

SUMMARY OF INVENTION

The present invention provides an illumination device including a light output unit having an output end that outputs illumination light; a diffusion layer that is disposed in a circumferential direction centered on a predetermined axis and that receives the illumination light from the output end, guides the illumination light while diffusing the illumination light, and outputs the illumination light from a surface thereof; and a reflective layer that is provided adjacent to a surface of the diffusion layer at an inner side in a radial direction and that reflects the illumination light outward in the radial direction. The diffusion layer contains a light guide material that guides the illumination light and a diffusion material dispersed and supported in the light guide material.

DESCRIPTION OF EMBODIMENTS

First Embodiment

An illumination device 100 according to a first embodiment of the present invention will be described below with reference to FIGS. 1A to 5.

Figure 1A:
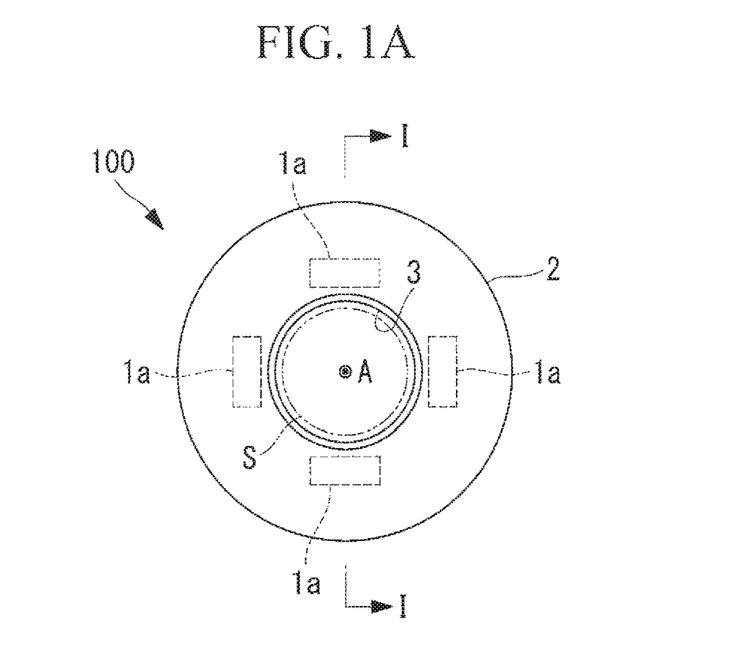
FIG. 1A is a front view showing the overall configuration of an illumination device according to a first embodiment of the present invention.
Figure 1B:
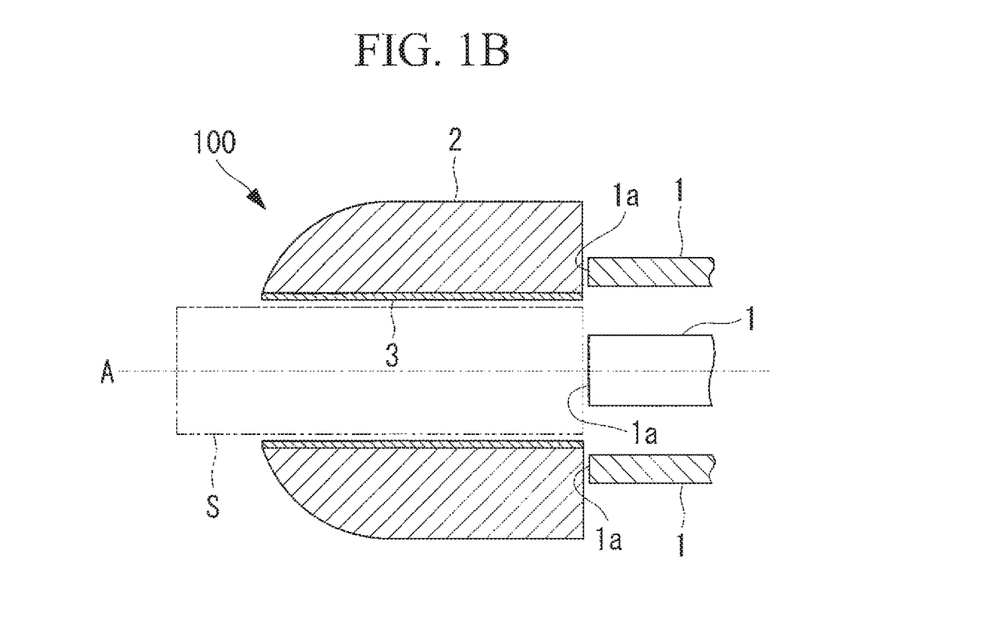
FIG. 1B is a longitudinal sectional view, taken along line I-I, of the illumination device in FIG. 1A.

As shown in FIGS. 1A and 1B, the distal-end portion of the illumination device 100 according to this embodiment (i.e., a portion composed of a diffusion layer 2 and a reflective layer 3, described later) has a cylindrical structure and is exposed to the outside so as to circumferentially surround an image-capturing optical system provided at the distal end of an endoscope. In the same figures, the space S enclosed by the two-dot chain line represents the space were the image-capturing optical system is disposed, and the axis A represents the observation optical axis of the image-capturing optical system. In particular, the illumination device 100 according to this embodiment is designed for endoscopes including image-capturing optical systems having viewing, angles of 180° or more and capable of simultaneously capturing images of fields of view forward in the drawings, in the direction from right to left) and sideward of the observation optical axis A.

Specifically, as shown in FIGS. 1A and 1B, the illumination device 100 includes light output units 1 having output ends 1a that output illumination light, a substantially cylindrical diffusion layer 2 that is provided, at the distal ends of the light output units 1 and that receives the illumination light from the output ends 1a, guides the illumination light while diffusing it, and outputs the illumination light from a surface thereof, and a reflective layer 3 provided on the inner circumferential surface of the diffusion layer 2.

The light output units 1 are, for example, fiber bundles disposed inside the endoscope. The proximal ends of the fiber bundles are connected to a light source unit (not shown) disposed outside the endoscope, and illumination light supplied from the light source unit is guided through the fiber bundles and is output from the distal ends of the fiber bundles, i.e., from the output ends 1a. The output ends 1a are located opposite the proximal-end surface of the diffusion layer 2 in sufficient proximity thereto and direct the illumination light into the proximal-end surface of the diffusion layer 2.

The color of the illumination light may be selected, as appropriate, depending on the application, preferably white for normal observation of subjects. For special light observation such as narrow-band imaging (NBI) and fluoroscopy, the illumination light may be narrowband light, i.e., light having its emission spectrum only in a particular wavelength band.

Figure 2:
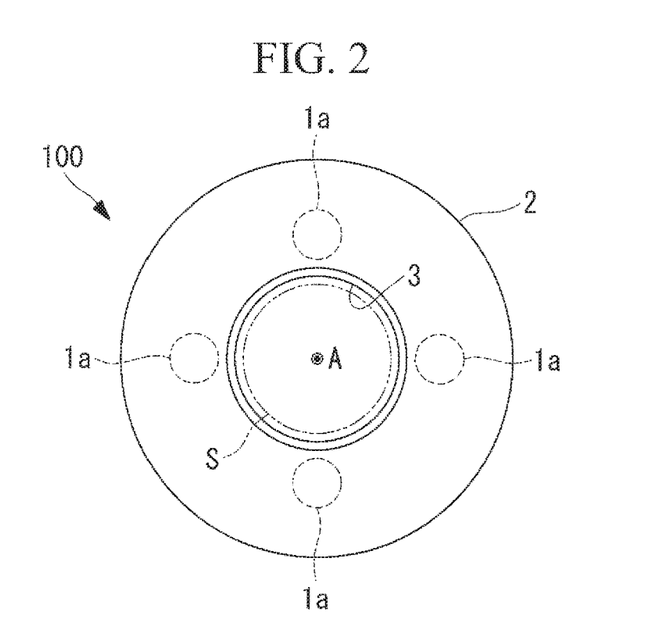
FIG. 2 is a front view of the illumination device, showing a modification of the shape of the output ends of the light output units in FIGS. 1A and 1B.
Figure 3:
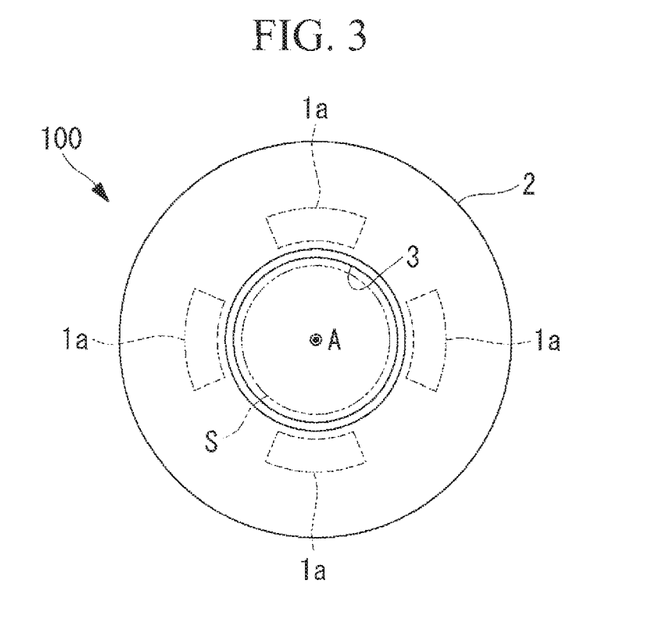
FIG. 3 is a front view of the illumination device, showing another modification of the shape of the output ends of the light output units in FIGS. 1A and 1B.

Although FIG. 1A illustrates four light output units 1 arranged at regular intervals on a circumference centered on the observation optical axis A, the arrangement and number of light output units 1 may be changed, as appropriate. The light output units 1 may be, for example, small solid-state light sources such as LEDs and lasers, rather than fiber bundles. The shape of the output ends 1a may also be changed, as appropriate. As shown in FIGS. 2 and 3, the output ends 1a may be circular or annular-sector-shaped, and they may also have other shapes, including ovals and polygons other than rectangles. This improves the design flexibility of the light output unit.

The diffusion layer 2 is disposed such that the central axis thereof (predetermined axis) is substantially in line with the observation optical axis (predetermined axis) A. A typical image-capturing optical system installed in the endoscope includes a plurality of lenses arranged in line along the observation optical axis A and a cylindrical frame holding the plurality of lenses inside. The diffusion layer 2 is disposed around the outer circumferential surface of the frame.

The diffusion layer 2 contains a light guide material through which the illumination light propagates and a diffusion material that diffuses the illumination light. The diffusion material is dispersed and supported at substantially uniform density in the light guide material, which serves as a matrix. Examples of light guide materials include plastic materials such as acrylic and ZEONOR, whereas examples of diffusion materials include titanium oxide.

Figure 4:
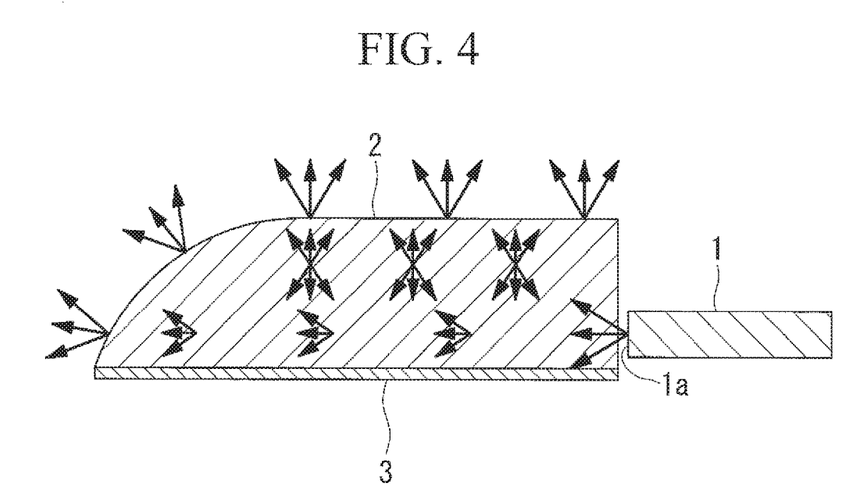
FIG. 4 illustrates the behavior of rays in the diffusion layer in FIGS. 1A and 1B.

As shown in FIG. 4, while the illumination light entering the proximal-end surface of the diffusion layer 2 is guided through the diffusion layer 2, the illumination light is substantially isotropically diffused by repeated refraction due to the difference in refractive index between the light guide material and the diffusion material and is thereby converted into substantially isotropically scattered light. The arrows in FIG. 4 indicate the rays contained in the illumination light and the directions in which the rays travel. Nearly all of the illumination light that has been converted into substantially isotropically scattered light is output to the outside from the surfaces of the diffusion layer 2 that are exposed to the outside, i.e., the distal-end surface and the outer circumferential surface, under the reflection effect of the reflective layer 3, described later. Thus, the illumination light output toward the front with respect to the observation optical axis A from the distal-end surface of the diffusion layer 2 mainly illuminates the forward field of view of the observation optical system, whereas the illumination light output in the radial directions with respect to the observation optical axis A from the outer circumferential surface of the diffusion layer 2 mainly illuminates the side field of view of the observation optical system over the entire circumference thereof.

The distal-end surface of the diffusion layer 2 has a conical shape that is smoothly continuous with the outer circumferential surface and that becomes gradually narrower toward the distal end, preferably a round conical shape. This allows the illumination light output from the distal-end surface and the outer circumferential surface to have uniform intensity at each angle and thus allows a wide field of view to be illuminated with uniform brightness at each position, thus providing good illumination performance.

The reflective layer 3 has a high reflectance for the illumination light and is provided adjacent to the inner circumferential surface of the diffusion layer 2. The reflective layer 3 may be a sheet or pipe fixed to the inner circumferential surface of the diffusion layer 2. The reflective layer 3 may be adjacent to the diffusion layer 2 with an air layer therebetween or may be fixed to the diffusion layer 2 with an optical adhesive having substantially the same refractive index as the diffusion layer 2. Alternatively, the reflective layer 3 may be a reflective film formed on the inner circumferential surface of the diffusion layer 2. The illumination light output from the inner circumferential surface of the diffusion layer 2 is reflected back into the diffusion layer 2 by the reflective layer 3; thus, nearly all of the illumination light entering the proximal-end surface of the diffusion layer 2 along the observation optical axis A is output from the distal-end surface and outer circumferential surface of the diffusion layer 2 and contributes to the illumination of the forward and side fields of view. This provides high illumination efficiency.

The operation of the thus-configured illumination device 100 will now be described.

In the illumination device 100 according to this embodiment, the illumination light directed from the output ends 1a of the light output units 1 into the diffusion layer 2 is guided through the diffusion layer 2 while being diffused in various directions. Some of the rays contained in the illumination light are output from the distal-end surface or outer circumferential surface of the diffusion layer 2. Other rays contained in the illumination light are output from the inner circumferential surface and are reflected back into the diffusion layer 2 by the reflective layer 3 disposed between the diffusion layer 2 and the image-capturing optical system; thus, they are repeatedly diffused by the diffusion layer 2 and reflected by the reflective layer 3 until they are output from the distal-end surface or the outer circumferential surface. In this way, the illumination light directed from the light output units 1 into the diffusion layer 2 can simultaneously illuminate the forward and side fields of view of the observation optical system with sufficient brightness and little intensity loss.

The illumination light that has been converted into isotropically scattered light by nearly complete diffusion (Lambertian scattering) in the diffusion layer 2 is output in various directions from the diffusion layer 2. In addition, the distal-end surface and the outer circumferential surface are smoothly continuous in shape. Thus, there is no discontinuous change in brightness between the illumination light output from the distal-end surface and the illumination light output from the outer circumferential surface. This allows illumination with uniform brightness over a wide angular range, i.e., 180° or more.

In this case, the illumination device 100 according to this embodiment is a cylindrical device disposed in a thin space around the image-capturing optical system installed in the endoscope so as to be coaxial with the image-capturing optical system and has a layered structure with a sufficiently small size in the radial direction of the endoscope. The illumination device 100 can thus be built into the distal end of the endoscope with little increase in the tip diameter of the endoscope. Specifically, the illumination device 100 built into the distal end of the endoscope increases the tip diameter of the endoscope only by the thickness of the cylindrical diffusion layer 2 and the reflective layer 3. The illumination device 100 is therefore advantageous in that it is suitable for use with thin endoscopes.

Figure 5:
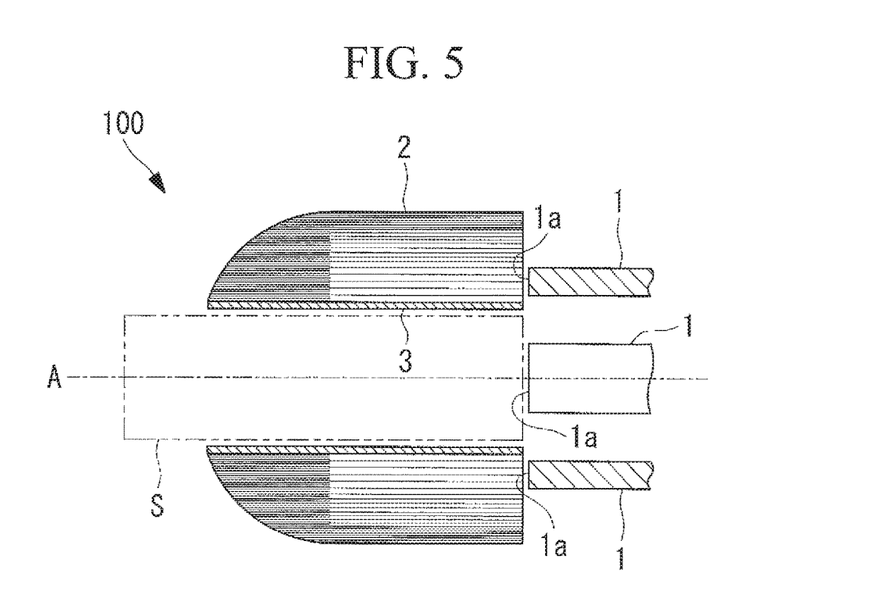
FIG. 5 is a longitudinal sectional view of the illumination device, showing a modification of the diffusion layer in FIGS. 1A and 1B.

Although the diffusion material is dispersed at uniform density in the diffusion layer 2 in this embodiment, the density of the diffusion material may instead be non-uniform in the diffusion layer 2. For example, as shown in FIG. 5, the diffusion layer 2 may have a gradient in the density of the diffusion material. In FIG. 5, the intervals between the horizontal hatching lines represent the density of the diffusion material; that is, smaller intervals between hatching lines indicate higher diffusion material densities. The gradient in the density of the diffusion material is formed such that the density of the diffusion material becomes lower toward the inner side in the radial direction, where the output ends 1a are located, and becomes higher toward the outer side in the radial direction. If the output ends 1a are located outside in the radial direction, the density of the diffusion material may be lower at the outer side in the radial direction and higher at the inner side in the radial direction.

The illumination light is also diffused backward (in the drawings, in the direction from left to right) with respect to the observation optical axis A in the diffusion layer 2. Specifically, a portion of the illumination light diffused by the diffusion layer 2, particularly near the output ends 1a, is output from the proximal-end surface of the diffusion layer 2, which results in a loss in intensity of the illumination light. Accordingly, as shown in FIG. 5, a gradient in the density of the diffusion material is created such that the density of the diffusion material is lower near the output ends 1a. This reduces the illumination light output from the diffusion layer 2 backward with respect to the observation optical axis A, thereby achieving a higher illumination efficiency.

Second Embodiment

An illumination device 200 according to a second embodiment of the present invention will now be described with reference to FIGS. 6 and 7. In this embodiment, the elements that differ from those of the first embodiment described above are mainly described, whereas the same elements as in the first embodiment are labeled with the same reference signs and are not described.

Figure 6:
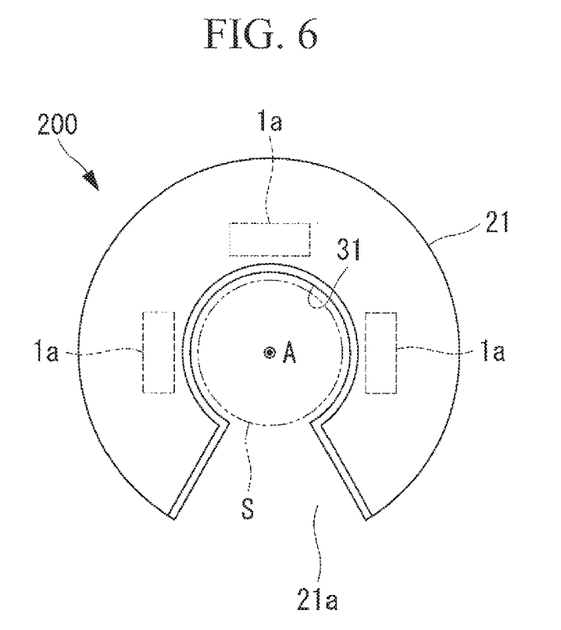
FIG. 6 is a front view showing the overall configuration of an illumination device according to a second embodiment of the present invention.
Figure 7:
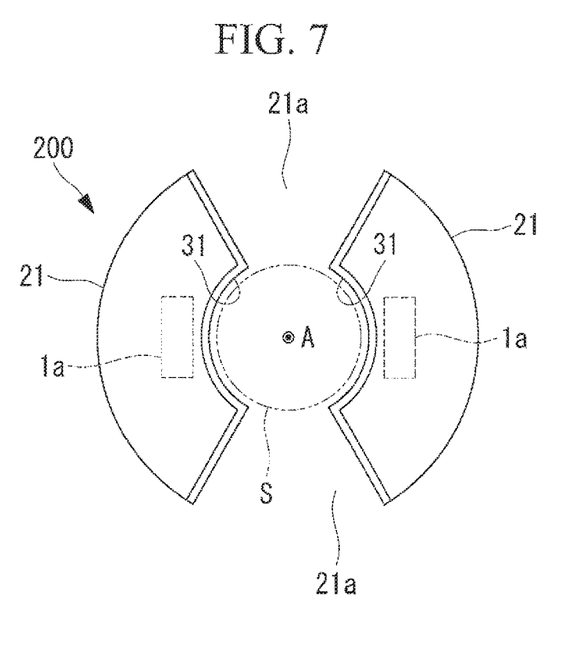
FIG. 7 is a front view of the illumination device, showing a modification of the shape of the diffusion layer in FIG. 6.

As shown in FIG. 6, the illumination device 200 according to this embodiment differs from the illumination device 100 according to the first embodiment mainly in that the illumination device 200 includes a diffusion layer 21 having an approximately C-shaped transverse cross-section formed by removing a portion extending in the circumferential direction, rather than the diffusion layer 2 extending over the entire circumference thereof.

A cutout 21a formed by removing, in the longitudinal direction, a portion of the diffusion layer 21 extending in the circumferential direction has an annular-sector-shaped transverse cross-section. The remaining configuration and operation of the diffusion layer 21 are similar to those of the diffusion layer 2 in the first embodiment.

A reflective layer 31 is provided on the inner circumferential surface of the diffusion layer 21, as the reflective layer 3 is in the first embodiment, to reflect the illumination light output from the inner circumferential surface back into the diffusion layer 21. Preferably, the reflective layer 31 is also provided on the sectional surfaces of the diffusion layer 21 exposed in the cutout 21a to reflect the illumination light output from the sectional surfaces back into the diffusion layer 21. The remaining configuration and operation of the reflective layer 31 are similar to those of the reflective layer 3 in the first embodiment.

Various components are disposed around the image-capturing optical system for design reasons. The illumination device 200 according to this embodiment allows such components to be installed in the space formed by the cutout 21a, which is advantageous in providing a more versatile structure. Another advantage is that, as in the first embodiment, the illumination device 200 allows effective and efficient illumination over a wide angular range, i.e., 180° or more, and is suitable for use with thin endoscopes.

In this embodiment, the shape and number of cutouts 21a may be changed, as appropriate. For example, the diffusion layer 21 may be divided into a plurality of diffusion layers 21 in the circumferential direction by forming a plurality of cutouts 21a in the circumferential direction. In this case, each diffusion layer 21 is substantially horseshoe-shaped. FIG. 7 illustrates an example where the diffusion layer 21 is divided into two members by forming two cutouts 21a in the circumferential direction.

As shown in FIGS. 2 and 3, the output ends 1a of the light output units 1 in this embodiment may have shapes other than rectangles.

As shown in FIG. 5, the diffusion layer 21 in this embodiment may have a gradient in the density of the diffusion material.

Third Embodiment

An illumination device 300 according to a third embodiment of the present invention will now be described with reference to FIGS. 8A to 9B. In this embodiment, the elements that differ from those of the first and second embodiments described above are mainly described, whereas the same elements as in the first and second embodiments are labeled with the same reference signs and are not described.

Figure 8A:
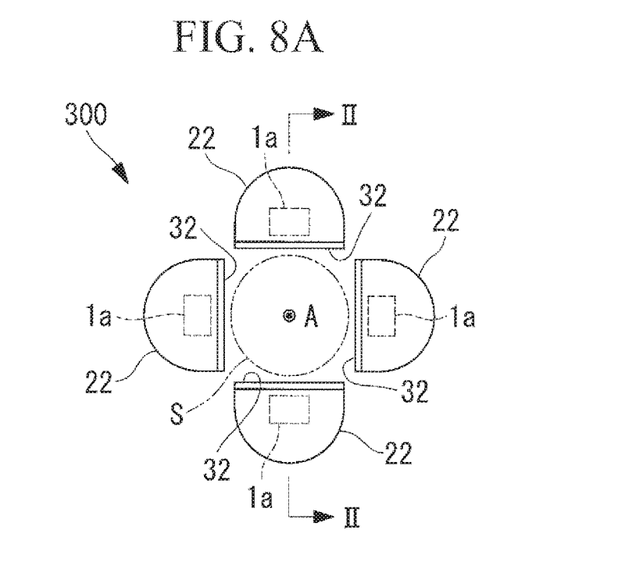
FIG. 8A is a front view showing the overall configuration of an illumination device according to a third embodiment of the present invention.
Figure 8B:
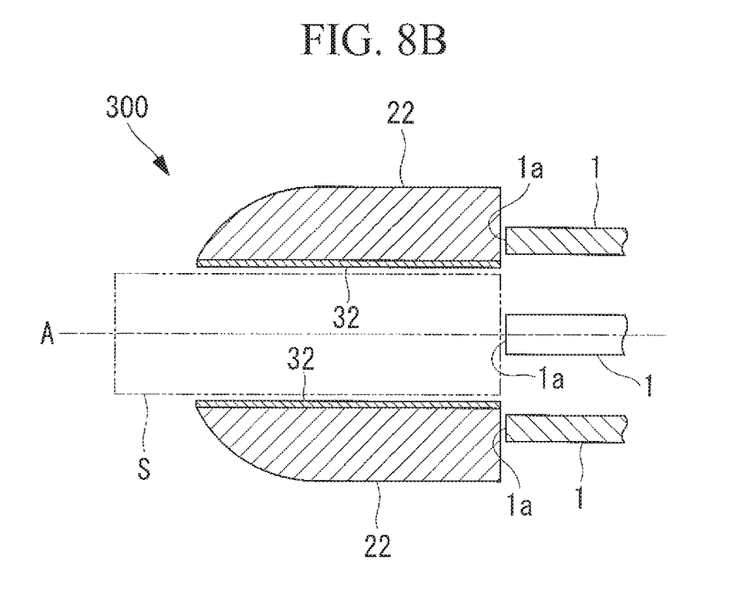
FIG. 8B is a longitudinal sectional view, taken along line II-II, of the illumination device in FIG. 8A.

As shown in FIGS. 8A and 8B, the illumination device 300 according to this embodiment differs from the illumination devices 100 and 200 according to the first and second embodiments mainly in that the illumination device 300 includes a plurality of (in this example, four) diffusion layers 22 arranged substantially at regular intervals in the circumferential direction centered on the observation optical axis A, rather than the cylindrical diffusion layers 2 and 21, and that the illumination device 300 includes four units each composed of a diffusion layer 22, a reflective layer 32, and a light output unit 1.

Each diffusion layer 22 is a substantially semicircular pillar member having a flat side surface at the inner side in the radial direction and a curved side surface at the outer side in the radial direction. The remaining configuration and operation of the diffusion layers 22 are similar to those of the diffusion layer 2 in the first embodiment.

The reflective layers 32 are provided on the flat side surfaces of the diffusion layers 22 and have a flat shape. The remaining configuration and operation of the reflective layers 32 are similar to those of the reflective layer 3 in the first embodiment.

The thus-configured illumination device 300 according to this embodiment, which includes the four separate diffusion layers 22, is advantageous in that the flat side surfaces of the diffusion layers 22 can be processed in any direction during the process of forming the reflective layers 32 on the diffusion layers 22 and that the reflective layers 32, which have a flat shape, are easier to form than the reflective layers 3 and 31 described above. Another advantage is that, as in the first embodiment, the illumination device 300 allows effective and efficient illumination over a wide angular range, i.e., 180° or more, and is suitable for use with thin endoscopes.

Figure 9A:
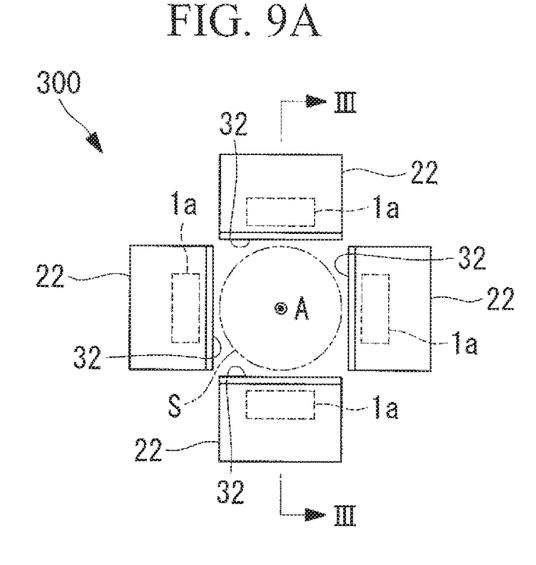
FIG. 9A is a front view of the illumination device, showing a modification the shape of the diffusion layer in FIGS. 8A and 8B.
Figure 9B:
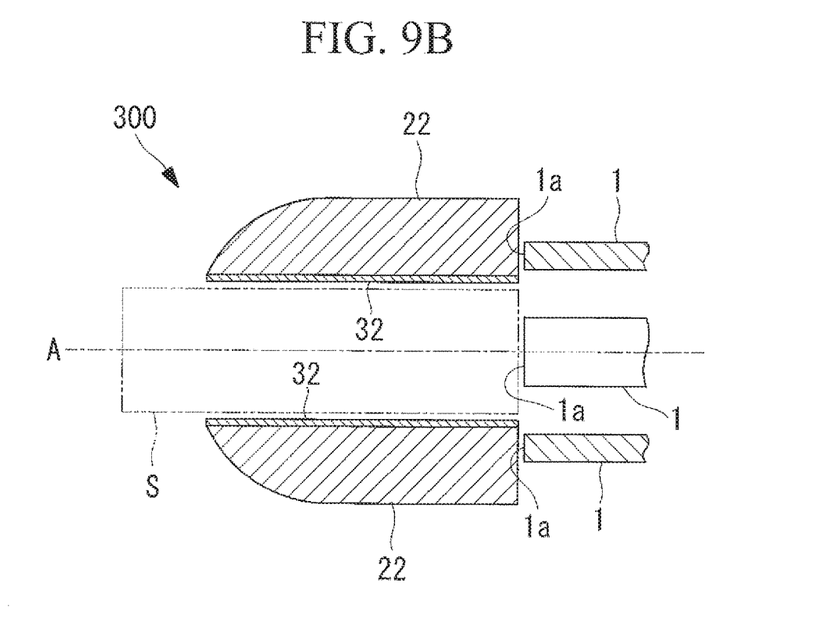
FIG. 9B is a longitudinal sectional view, taken along line III-III, of the illumination device in FIG. 9A.

In this embodiment, the diffusion layers 22 may have any pillar shape with a flat side surface at the inner side in the radial direction. For example, as shown in FIGS. 9A and 9B, the diffusion layers 22 may have a quadrangular prism shape with a rectangular transverse cross-section.

As shown in FIGS. 2 and 3, the output ends 1a of the light output units 1 in this embodiment may have shapes other than rectangles.

As shown in FIG. 5, the diffusion layers 22 in this embodiment may have a gradient in the density of the diffusion material.

Fourth Embodiment

An illumination device 400 according to a fourth embodiment of the present invention will now be described with reference to FIGS. 10A to 10B. In this embodiment, the elements that differ from those of the first to third embodiments described above are mainly described, whereas the same elements as in the first to third embodiments are labeled with the same reference signs and are not described.

Figure 10A:
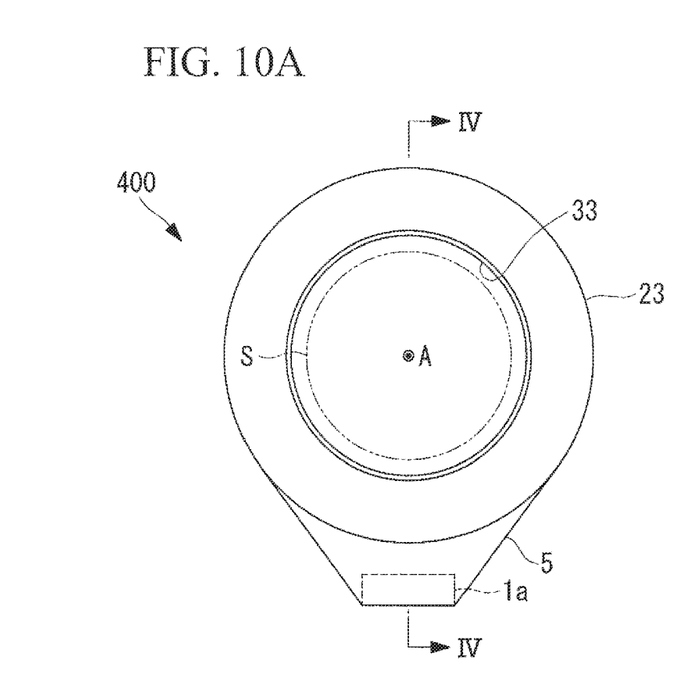
FIG. 10A is a front view showing the overall configuration of an illumination device according to a fourth embodiment of the present invention.
Figure 10B:
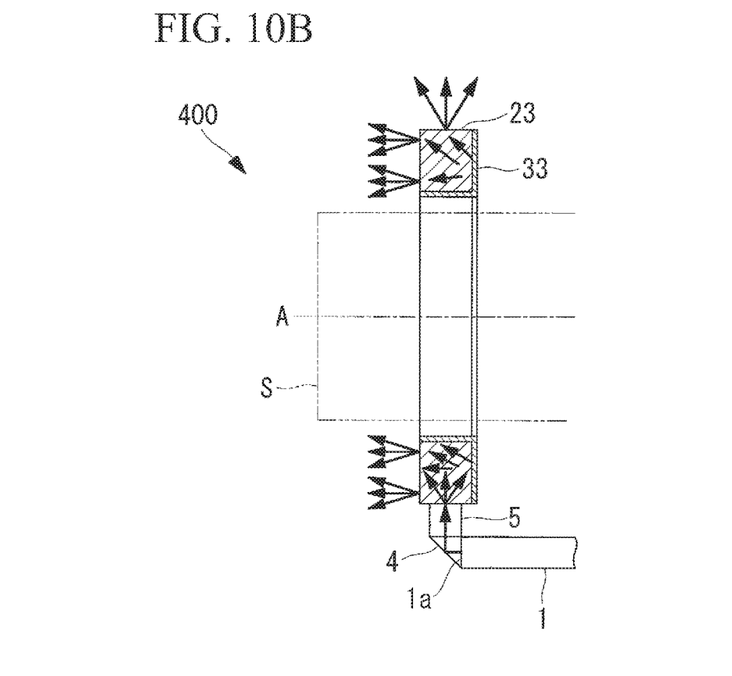
FIG. 10B is a longitudinal sectional view, taken along line IV-IV, of the illumination device in FIG. 10A.

As shown in FIGS. 10A and 10B, the illumination device 400 according to this embodiment differs from the illumination devices 100 to 300 according to the first to third embodiments mainly in that the light output unit 1 directs illumination light into the side of a diffusion layer 23, rather than into the proximal end of the diffusion layer 2, 21, or 22.

In this embodiment, the diffusion layer 23 is a ring-shaped member having a smaller size in the observation optical axis A direction than the diffusion layer 2. The remaining configuration and operation of the diffusion layer 23 are similar to those of the diffusion layer 2 in the first embodiment.

Disposed outside the diffusion layer 23 in the radial direction are a deflection prism 4 that deflects the illumination light output parallel to the observation optical axis A from the output end 1a of the light output unit 1 by 90° toward the outer circumferential surface of the diffusion layer 23 and a light guide member 5 that loins the output surface of the deflection prism 4 to a portion of the outer circumferential surface of the diffusion layer 23.

A reflective layer 33 is provided on the inner circumferential surface and the proximal-end surface of the ring-shaped diffusion layer 23 and reflects the illumination light output from the inner circumferential surface or the proximal-end surface back into the diffusion layer 23 so that substantially all of the illumination light entering the diffusion layer 23 is output from the distal-end surface and the outer circumferential surface of the diffusion layer 23.

In the thus-configured illumination device 400 according to this embodiment, the illumination light output from the output end 1a is deflected by the deflection prism 4 to enter a portion of the outer circumferential surface of the diffusion layer 23 through the light guide member 5. As in the first embodiment, the illumination light is converted into substantially isotropically scattered light by the diffusion layer 23 and is output to the outside from the distal-end surface and the outer circumferential surface of the diffusion layer 23 under the reflection effect of the reflective layer 33. The illumination light is also guided through the diffusion layer 23 in the circumferential direction while being repeatedly diffused by the diffusion layer 23 and reflected by the reflective layer 33 and is thereby output from the entire circumference of the diffusion layer 23.

The thus-configured illumination device 400 according to this embodiment is advantageous in that, as in the first embodiment, it allows effective and efficient illumination over a wide angular range, i.e., 180° or more, and is suitable for use with thin endoscopes.

As shown in FIGS. 2 and 3, the output end 1a of the light output unit 1 in this embodiment may have shapes other than rectangles.

As shown in FIG. 5, the diffusion layer 23 in this embodiment may have a gradient in the density of the diffusion material, such that the density of the diffusion material is lower at and near the position where the illumination light enters the diffusion layer 23.

The invention claimed is:

1. An illumination device comprising:
   a light output unit having an output end that outputs illumination light;
   a diffusion layer that is disposed in a circumferential direction centered on a predetermined axis and that receives the illumination light from the output end, guides the illumination light while diffusing the illumination light, and outputs the illumination light from a surface thereof; and
   a reflective layer that is provided adjacent to a surface of the diffusion layer at an inner side in a radial direction and that reflects the illumination light outward in the radial direction,
   wherein the diffusion layer comprises a light guide material that guides the illumination light and a diffusion material dispersed and supported in the light guide material, and
   the diffusion layer is a substantially cylindrical member having a cutout formed by removing, in a longitudinal direction, a portion extending in the circumferential direction.

2. The illumination device according to claim 1, wherein the output end is circular, oval, polygonal, or annular-sector-shaped.

3. The illumination device according to claim 2, wherein the diffusion layer is a substantially cylindrical member having a cutout formed by removing, in a longitudinal direction, a portion extending in the circumferential direction.

4. The illumination device according to claim 3, wherein
the diffusion layer is divided into a plurality of diffusion layers arranged in the circumferential direction centered on the predetermined axis, and
each diffusion layer is substantially horseshoe-shaped.

5. The illumination device according to claim 2, comprising a plurality of the diffusion layers arranged in the circumferential direction,
wherein each diffusion layer is a pillar member having a flat side surface at the inner side in the radial direction, and
the reflective layer is provided on the flat side surface.

6. The illumination device according to claim 2, wherein the diffusion layer is ring-shaped.

7. The illumination device according to claim 2, wherein the density of the diffusion material is non-uniform in the diffusion layer.

8. The illumination device according to claim 2, wherein the diffusion layer has an outer circumferential surface and a distal-end surface having a conical shape that is smoothly continuous with the outer circumferential surface and that becomes gradually narrower toward a distal end.

9. The illumination device according to claim 1, wherein the diffusion layer is ring-shaped.

10. The illumination device according to claim 1, wherein
the diffusion layer is divided into a plurality of diffusion layers arranged in the circumferential direction centered on the predetermined axis, and
each diffusion layer is substantially horseshoe-shaped.

11. The illumination device according to claim 1, wherein the density of the diffusion material is non-uniform in the diffusion layer.

12. The illumination device according to claim 1, wherein the diffusion layer has an outer circumferential surface and a distal-end surface having a conical shape that is smoothly continuous with the outer circumferential surface and that becomes gradually narrower toward a distal end.

13. An illumination device comprising:
a light output unit having an output end that outputs illumination light;
a diffusion layer that is disposed in a circumferential direction centered on a predetermined axis and that receives the illumination light from the output end, guides the illumination light while diffusing the illumination light, and outputs the illumination light from a surface thereof;
a reflective layer that is provided adjacent to a surface of the diffusion layer at an inner side in a radial direction and that reflects the illumination light outward in the radial direction; and
a plurality of the diffusion layers arranged in the circumferential direction,
wherein the diffusion layer comprises a light guide material that guides the illumination light and a diffusion material dispersed and supported in the light guide material,
each diffusion layer is a pillar member having a flat side surface at the inner side in the radial direction, and
the reflective layer is provided on the flat side surface.

14. The illumination device according to claim 13, wherein the output end is circular, oval, polygonal, or annular-sector-shaped.

15. The illumination device according to claim 14, wherein the diffusion layer is a substantially cylindrical member having a cutout formed by removing, in a longitudinal direction, a portion extending in the circumferential direction.

16. The illumination device according to claim 15, wherein
the diffusion layer is divided into a plurality of diffusion layers arranged in the circumferential direction centered on the predetermined axis, and
each diffusion layer is substantially horseshoe-shaped.

17. The illumination device according to claim 14, comprising a plurality of the diffusion layers arranged in the circumferential direction,
wherein each diffusion layer is a pillar member having a flat side surface at the inner side in the radial direction, and
the reflective layer is provided on the flat side surface.

18. The illumination device according to claim 14, wherein the diffusion layer is ring-shaped.

19. The illumination device according to claim 14, wherein the density of the diffusion material is non-uniform in the diffusion layer.

20. The illumination device according to claim 14, wherein the diffusion layer has an outer circumferential surface and a distal-end surface having a conical shape that is smoothly continuous with the outer circumferential surface and that becomes gradually narrower toward a distal end.

21. The illumination device according to claim 13, wherein the diffusion layer is ring-shaped.

22. The illumination device according to claim 13, wherein the density of the diffusion material is non-uniform in the diffusion layer.

23. The illumination device according to claim 13, wherein the diffusion layer has an outer circumferential surface and a distal-end surface having a conical shape that is smoothly continuous with the outer circumferential surface and that becomes gradually narrower toward a distal end.

* * * * *